United States Patent
Maschino et al.

(10) Patent No.: US 12,059,333 B2
(45) Date of Patent: Aug. 13, 2024

(54) APERTURED EXTRUSION COATED NONWOVEN WEB FOR ABSORBENT ARTICLES AND ABSORBENT ARTICLES INCLUDING SAME

(71) Applicant: FITESA FILM PRODUCTS LLC, Simpsonville, SC (US)

(72) Inventors: Andrew D. Maschino, Paris, IL (US); Brian C. Loomis, Terre Haute, IN (US); Todd R. Skochdopole, Moseley, VA (US); Paul Eugene Thomas, Terre Haute, IN (US)

(73) Assignee: FITESA FILM PRODUCTS LLC, Simpsonville, SC (US)

( * ) Notice: Subject to any disclaimer, the term of this patent is extended or adjusted under 35 U.S.C. 154(b) by 968 days.

(21) Appl. No.: 16/854,085

(22) Filed: Apr. 21, 2020

(65) Prior Publication Data
US 2020/0330292 A1    Oct. 22, 2020

Related U.S. Application Data

(60) Provisional application No. 62/836,989, filed on Apr. 22, 2019.

(51) Int. Cl.
*A61F 13/15* (2006.01)
*A61F 13/511* (2006.01)
(Continued)

(52) U.S. Cl.
CPC .... *A61F 13/5123* (2013.01); *A61F 13/15203* (2013.01); *A61F 13/15699* (2013.01);
(Continued)

(58) Field of Classification Search
CPC ............ A61F 13/5123; A61F 13/15203; A61F 13/15699; A61F 13/581104;
(Continued)

(56) References Cited

U.S. PATENT DOCUMENTS

| 3,945,386 A | 3/1976 | Anczurowski et al. |
| 4,151,240 A | 4/1979 | Lucas et al. |

(Continued)

FOREIGN PATENT DOCUMENTS

| CN | 1251551 A | 4/2000 |
| CN | 102292056 A | 12/2011 |

(Continued)

OTHER PUBLICATIONS

Indian Office Action dated Sep. 7, 2022, for Indian Patent Application No. 202117046711.
(Continued)

*Primary Examiner* — Jacqueline F Stephens
(74) *Attorney, Agent, or Firm* — KARCESKI IP LAW, PLLC

(57) ABSTRACT

An apertured extrusion coated nonwoven web for use as a topsheet in an absorbent article includes a nonwoven material having a user-facing side and a garment-facing side opposite the user-facing side. The nonwoven material includes a plurality of fibers. The apertured extrusion coated nonwoven web also includes a polymer coating on the garment-facing side of the nonwoven material, the polymer coating having a basis weight of about 2 gsm to about 6 gsm, and a plurality of three-dimensional apertures that extend through the nonwoven material and the polymer coating. Each of the plurality of three-dimensional apertures includes a continuous sidewall extending from a garment-facing side of the polymer coating. The apertured extrusion coated nonwoven web has an open area of greater than 5% when subjected to a pressure of 0.6 psi.

16 Claims, 12 Drawing Sheets

(51) Int. Cl.
  *A61F 13/512* (2006.01)
  *A61L 15/26* (2006.01)
  *B29C 59/04* (2006.01)
  *A61F 13/51* (2006.01)
  *B29K 105/08* (2006.01)
  *B29L 31/48* (2006.01)

(52) U.S. Cl.
  CPC ......... *A61F 13/51104* (2013.01); *A61L 15/26* (2013.01); *B29C 59/046* (2013.01); *A61F 2013/15406* (2013.01); *A61F 2013/51059* (2013.01); *A61F 2013/51165* (2013.01); *B29K 2105/0854* (2013.01); *B29L 2031/4878* (2013.01)

(58) Field of Classification Search
  CPC .. A61F 2013/15406; A61F 2013/51059; A61F 2013/51165; B29C 59/046; A61L 15/26; B29K 2105/0854; B29L 2031/4878
  See application file for complete search history.

(56) References Cited

U.S. PATENT DOCUMENTS

| | | | |
|---|---|---|---|
| 4,324,247 A | 4/1982 | Aziz | |
| 4,456,570 A | 6/1984 | Thomas et al. | |
| 4,629,643 A | 12/1986 | Curro et al. | |
| 4,726,976 A | 2/1988 | Karami et al. | |
| 4,995,930 A | 2/1991 | Merz et al. | |
| 5,536,555 A | 7/1996 | Zelazoski et al. | |
| 5,919,177 A | 7/1999 | Georger et al. | |
| 5,935,682 A | 8/1999 | Wallstrom | |
| 6,075,179 A | 6/2000 | McCormack et al. | |
| 6,211,102 B1 | 4/2001 | Jones et al. | |
| 6,242,074 B1 | 6/2001 | Thomas | |
| 6,309,736 B1 | 10/2001 | McCormack et al. | |
| 6,610,904 B1 | 8/2003 | Thomas et al. | |
| 6,638,636 B2 | 10/2003 | Tucker | |
| 6,764,566 B1 | 7/2004 | Griesbach, III et al. | |
| 6,849,319 B2 * | 2/2005 | Cree | B26F 1/24 428/137 |
| 6,989,187 B2 * | 1/2006 | Thomas | B32B 3/266 428/167 |
| 7,198,836 B2 * | 4/2007 | Thomas | B32B 3/266 428/167 |
| 7,204,907 B2 | 4/2007 | Cree et al. | |
| 7,351,297 B2 | 4/2008 | Middlesworth et al. | |
| 7,364,687 B2 | 4/2008 | Maschino et al. | |
| 7,601,415 B2 | 10/2009 | Cree et al. | |
| 8,613,736 B2 | 12/2013 | Schnabel et al. | |
| 8,937,211 B2 | 1/2015 | Dent et al. | |
| 9,115,449 B2 | 8/2015 | Burckhardt et al. | |
| 9,849,602 B2 | 12/2017 | Cree | |
| 10,258,517 B1 * | 4/2019 | Maschino | B32B 3/30 |
| 2004/0122396 A1 | 6/2004 | Maldonado et al. | |
| 2005/0124949 A1 | 6/2005 | Steffen et al. | |
| 2011/0151185 A1 | 6/2011 | Cree | |
| 2014/0128828 A1 | 5/2014 | Andersson et al. | |
| 2017/0087029 A1 | 3/2017 | Nelson et al. | |
| 2018/0104842 A1 * | 4/2018 | Cree | B32B 27/20 |
| 2018/0256414 A1 * | 9/2018 | Maschino | B29C 41/50 |

FOREIGN PATENT DOCUMENTS

| | | |
|---|---|---|
| CN | 102762375 A | 10/2012 |
| CN | 105208988 A | 12/2015 |
| DE | 4016348 A1 | 11/1991 |
| JP | H07501244 A | 2/1995 |
| JP | 2001170110 A | 6/2001 |
| JP | 2005177086 A | 7/2005 |
| JP | 2011515593 A | 5/2011 |

OTHER PUBLICATIONS

International Preliminary Report on Patentability dated Nov. 4, 2021, for International Patent Application No. PCT/US2020/029078.
International Search Report and Written Opinion dated Jul. 6, 2020, for International Patent Application No. PCT/US2020/029078.
1 Chinese Office Action dated Dec. 7, 2022, for Chinese Patent Application No. 202080039247.8.
Chinese Office Action dated Jun. 23, 2022, for Chinese Patent Application No. 202080039247.8.
Chinese Office Action dated Mar. 25, 2023, for Chinese Patent Application No. 202080039247.8.
Japanese Office Action dated Aug. 25, 2023, for Japanese Patent Application No. 2021-562895.

\* cited by examiner

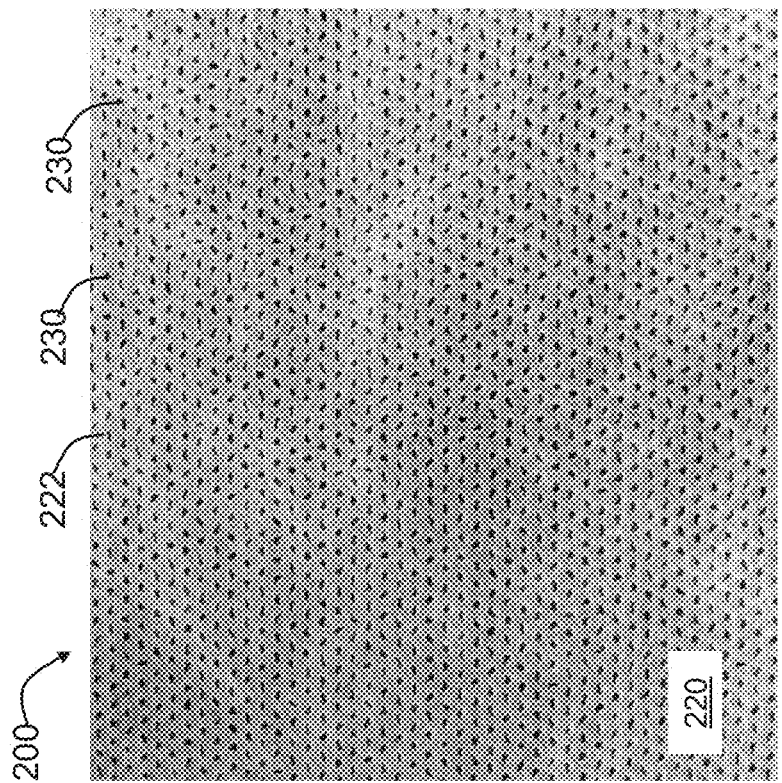
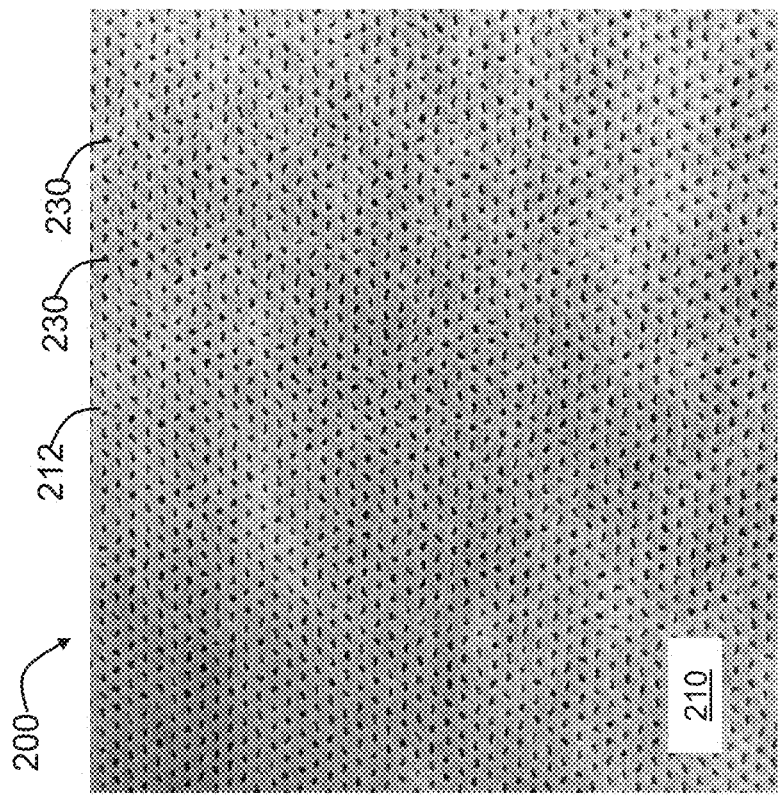
FIG. 2A
FIG. 2B

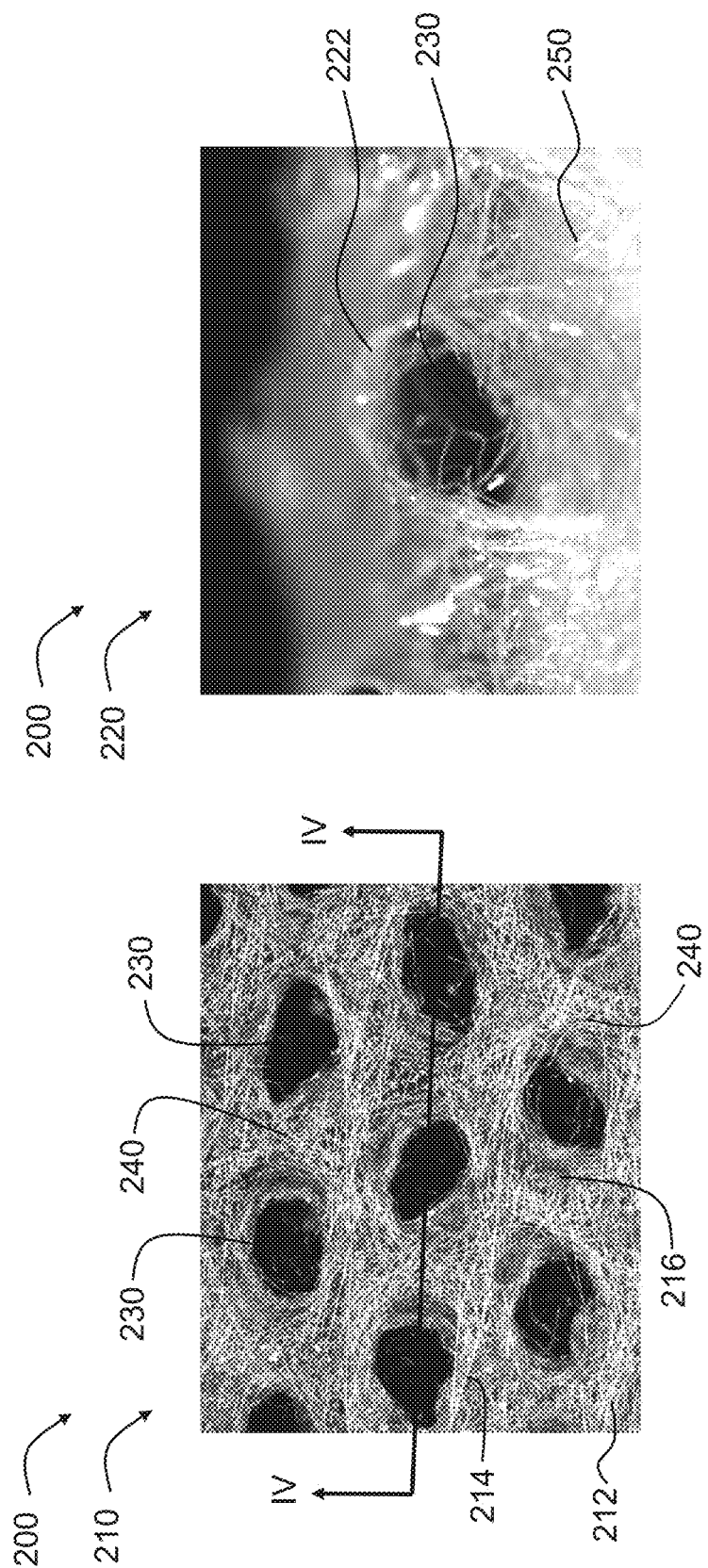

APERTURED EXTRUSION COATED NONWOVEN WEB FOR ABSORBENT ARTICLES AND ABSORBENT ARTICLES INCLUDING SAME

CROSS-REFERENCE TO RELATED APPLICATIONS

This application claims the benefit of priority from U.S. Provisional Patent Application No. 62/836,989, filed Apr. 22, 2019, the entire content of which is incorporated herein by reference.

FIELD

The present invention is directed to an apertured extrusion coated nonwoven web for absorbent articles and absorbent articles that include the apertured extrusion coated nonwoven web.

BACKGROUND

A variety of well-known absorbent articles are configured to absorb body fluids. Examples of such absorbent articles include, but are not limited to, feminine hygiene products, such as sanitary napkins, baby diapers, adult incontinence products, and bandages. A typical absorbent article is generally constructed with a fluid permeable user-facing topsheet, which may be a three dimensional apertured polymer film or a nonwoven web or a film/nonwoven laminate, an absorbent core, and a fluid impermeable garment or outwardly-facing backsheet, which may be a solid polymer film, for example.

Nonwoven materials are often used as topsheet components of such absorbent articles when it is desirable to achieve softness due to the contact of the topsheet with the skin of the wearer of the absorbent article, such as in a baby diaper. Although topsheets that are made from polymer films typically have better fluid handling performance characteristics when used in the absorbent article as compared to topsheets that are made from nonwoven materials, a topsheet made from a polymer film may have a visual appearance that is higher in gloss and therefore may be more "plastic-looking" than a nonwoven topsheet. Additionally, a polymer film topsheet may feel more "sticky" or "tacky" to the wearer than a nonwoven topsheet.

It is desirable to have a lightweight web that may be used in an absorbent article as, for example, a topsheet that has softness attributes more closely associated with a nonwoven material and performance attributes more closely associated with a three dimensional apertured polymer film.

SUMMARY

According to an aspect of the invention, there is provided an apertured extrusion coated nonwoven web for use as a topsheet in an absorbent article. The apertured extrusion coated nonwoven web includes a nonwoven material having a user-facing side and a garment-facing side opposite the user-facing side. The nonwoven material includes a plurality of fibers. The apertured extrusion coated nonwoven web also includes a polymer coating on the garment-facing side of the nonwoven material. The polymer coating has a basis weight of about 2 gsm to about 6 gsm. A plurality of three-dimensional apertures extend through the nonwoven material and the polymer coating. Each of the plurality of three-dimensional apertures includes a continuous sidewall extending from a garment-facing side of the polymer coating. The apertured extrusion coated nonwoven web has an open area of greater than 5% when subjected to a pressure of 0.6 psi.

In an embodiment, the apertured extrusion coated nonwoven web has an open area of at least 50% of an original open area after the pressure of 0.6 psi is decreased to 0.0 psi.

In an embodiment, the apertured extrusion coated nonwoven web has an original open area of about 9% to about 15%.

In an embodiment, the nonwoven material is a spunbond nonwoven material and the fibers are continuous fibers.

In an embodiment, the nonwoven material is a carded nonwoven material and the fibers are staple fibers.

In an embodiment, the nonwoven material has a basis weight of about 8 gsm to about 20 gsm. In an embodiment, the nonwoven material has a basis weight of about 10 gsm to about 15 gsm.

In an embodiment, the polymer coating includes polyethylene. In an embodiment, the polymer coating includes high density polyethylene.

In an embodiment, the polymer coating has a basis weight of about 4 gsm to about 6 gsm.

In an embodiment, the three-dimensional apertures are arranged in a pattern of about 5 mesh to about 30 mesh. In an embodiment, the three-dimensional apertures are arranged in a pattern of about 10 mesh to about 15 mesh.

According to an aspect of the invention, there is provided an absorbent article that includes a user-facing topsheet, a garment-facing backsheet, and an absorbent core in between the topsheet and the backsheet. The topsheet includes an apertured extrusion coated nonwoven web. The apertured extrusion coated nonwoven web includes a nonwoven material having a user-facing side and a garment-facing side opposite the user-facing side. The nonwoven material includes a plurality of fibers. The apertured extrusion coated nonwoven web also includes a polymer coating on the garment-facing side of the nonwoven material. The polymer coating has a basis weight of about 2 gsm to about 6 gsm. A plurality of three-dimensional apertures extend through the nonwoven material and the polymer coating. Each of the plurality of three-dimensional apertures includes a continuous sidewall extending from a garment-facing side of the polymer coating. The apertured extrusion coated nonwoven web has an open area of greater than 5% when subjected to a pressure of 0.6 psi.

According to an aspect of the invention, there is provided a method for making apertured extrusion coated nonwoven web for use as a topsheet in an absorbent article. The method includes extruding a polymer coating having a basis weight of about 2 gsm to about 6 gsm onto a nonwoven material to form an extrusion coated nonwoven web, and pin punching a plurality of three-dimensional apertures through the extrusion coated nonwoven web to form an apertured extrusion coated nonwoven web. Each of the plurality of three-dimensional apertures includes a continuous sidewall extending from a garment-facing side of the polymer coating. The apertured extrusion coated nonwoven web has an open area of greater than 5% when subjected to a pressure of 0.6 psi.

In an embodiment, the polymer coating is extruded onto the nonwoven material as the nonwoven material is fed over a forming structure that rotates about a cylinder having a vacuum slot through which a vacuum is pulled.

In an embodiment, the method includes activating the apertured extrusion coated nonwoven web.

In an embodiment, the method includes embossing the apertured extrusion coated nonwoven web.

These and other aspects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

The components of the following figures are illustrated to emphasize the general principles of the present disclosure and are not necessarily drawn to scale. Reference characters designating corresponding components are repeated as necessary throughout the figures for the sake of consistency and clarity.

FIG. 2A illustrates a user-facing side of an apertured extrusion coated nonwoven web that may be used as a topsheet for the absorbent article of FIG. 1;

FIG. 2B illustrates a garment-facing side of the apertured extrusion coated nonwoven web of FIG. 2A;

FIG. 3A is an enlarged view of a portion of the user-facing side of the apertured extrusion coated nonwoven web of FIG. 2A;

FIG. 3B is an enlarged view of a portion of the garment-facing side of the apertured extrusion coated nonwoven web of FIG. 2B;

DETAILED DESCRIPTION

Various embodiments of the present invention will now be highlighted. The discussion of any one embodiment is not intended to limit the scope of the present invention. To the contrary, aspects of the embodiments are intended to emphasize the breadth of the invention, whether encompassed by the claims or not. Furthermore, any and all variations of the embodiments, now known or developed in the future, also are intended to fall within the scope of the invention.

Figure 1:
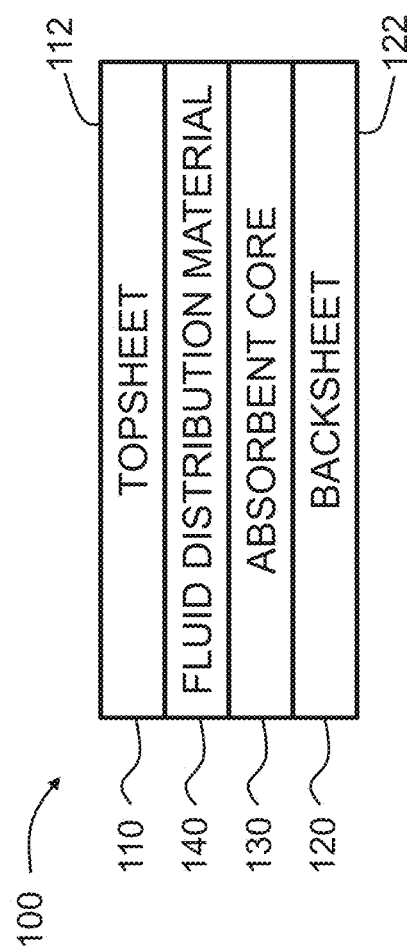
FIG. 1 schematically illustrates an absorbent article that includes a topsheet in accordance with an embodiment of the invention.

FIG. 1 schematically illustrates an absorbent article 100 in accordance with embodiments of the invention. As illustrated, the absorbent article 100 includes a topsheet 110 having a user facing surface 112, a backsheet 120 having a garment facing surface 122, and an absorbent core 130 positioned in between the topsheet 110 and the backsheet 120. The absorbent article 100 also optionally includes a fluid distribution material 140 positioned in between the topsheet 110 and the absorbent core 130. The topsheet 110, embodiments of which are described in further detail below, is permeable to fluids and is configured to face the user wearing the absorbent article 100 and contact the user's skin. The topsheet 110 receives insults of fluid from the user, and the fluid passes through the topsheet 110 to the fluid distribution material 140 (or straight to the absorbent core 130 in embodiments without a fluid distribution material 140). The fluid distribution material 140 is also permeable and is configured to receive the fluid from the topsheet 110 and distribute the fluid to the absorbent core 130. The absorbent core 130, which includes absorbent materials, receives the fluid from the fluid distribution material 140 (or straight from the topsheet 110) and stores the fluid until the absorbent article 100 is discarded. The backsheet 120, which is impermeable to liquid and may be in the form of a polymer film or laminate of a polymer film and nonwoven web, prevents liquid and other body exudates captured within the absorbent core 130 from leaking out of the absorbent article 100. The backsheet 120 may be breathable so that air, but not liquid, may pass through.

FIGS. 2A and 2B illustrate opposite sides of an apertured extrusion coated nonwoven web 200, which may be used as the topsheet 110 of FIG. 1, in accordance with an embodiment of the invention. FIG. 2A illustrates a user-facing side 210 of the extrusion coated nonwoven web 200, and FIG. 2B illustrates a garment-facing side 220 of the apertured extrusion coated nonwoven web 200. The user-facing side 210 includes a nonwoven material 212, and the garment-facing side 220 includes a polymer coating 222. A plurality of apertures 230 extend through the apertured extrusion coated nonwoven web 200, as illustrated.

FIG. 3A is an enlarged view of the user-facing side 210 of the apertured extrusion coated nonwoven web 200, and FIG. 3B is an enlarged view of the garment-facing side 220 of the apertured extrusion coated nonwoven web 200. As illustrated, the nonwoven material 212 on the user-facing side 210 includes a plurality of fibers 214 and a plurality of bonds 216 that bond the plurality of fibers 214 together. In the embodiment illustrated in FIGS. 2A, 2B, 3A and 3B, the nonwoven material 212 is a spunbond nonwoven material and the fibers 214 are continuous fibers.

As illustrated in FIG. 3A, the user-facing side 210 also includes a continuous land area 240 in between the plurality of apertures 230. When a user is wearing the absorbent article that includes the apertured extrusion coated material 200 as the topsheet 110, the continuous land area 240 contacts the user's skin. Because the continuous land area 240 is made up of the plurality of fibers 214, the apertured extrusion coated material 200 should feel soft to the user. As illustrated in FIG. 3B, the garment-facing side 220 also includes a continuous land area 250, which includes the polymer coating 222. The polymer coating 222 functions to block liquids that have passed through the plurality of apertures 230 from passing through the continuous land area 250 to the user.

The polymer coating 222 adheres to the fibers 214 of the nonwoven material 212 located at or near a garment-facing surface of the nonwoven material 212. In an embodiment, the polymer coating 222 may coat individual fibers 214 such that greater than 50% of the circumferential surface area of portions of individual fibers are coated by the polymer coating 222. Such an engagement between the polymer coating 222 and the fibers 214 of the nonwoven material 212 may provide a suitable bond between the two materials, which may prevent delamination of the two materials when the extrusion coated nonwoven material is later apertured, as described in further detail below.

Figure 4:
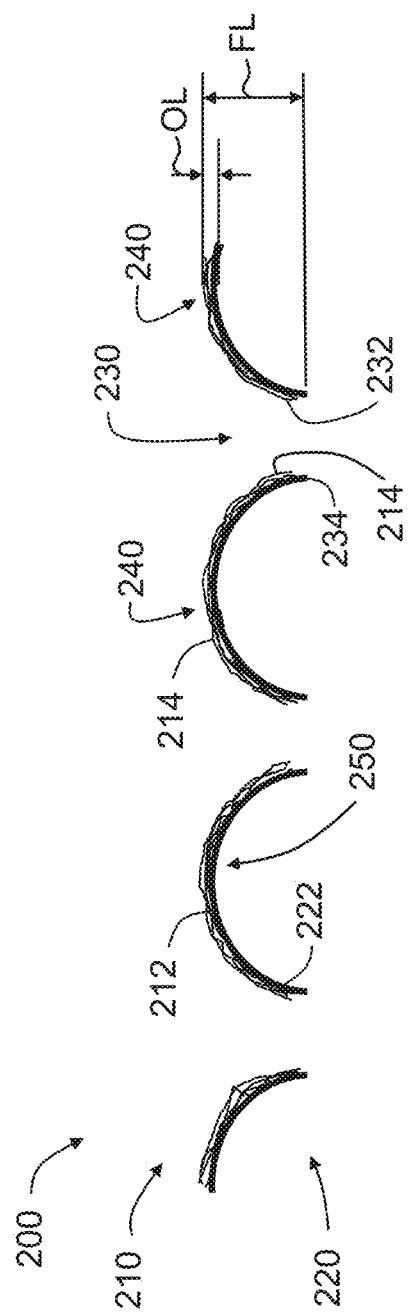
FIG. 4 is a schematic illustration of a cross-section of the apertured extrusion coated nonwoven web of FIG. 3A taken along line IV-IV.

FIG. 4 is a schematic cross-sectional view of the apertured extrusion coated nonwoven material 200 taken along line IV-IV in FIG. 3A. As illustrated, the plurality of apertures 230 are three-dimensional apertures that each has a sidewall 232 extending from the land area 240 of the user-facing side 210 to a distal tip 234, and fibers 214 of the nonwoven material 212 extend into the three-dimensional apertures 230. The three-dimensional apertures 230 provide the apertured extrusion coated nonwoven material 200 with a final loft FL that is greater that an original loft OL of the extrusion coated nonwoven material before the material is apertured, as described in further detail below.

One potential advantage of having three-dimensional apertures 230 that provide a final loft FL that is greater than the original loft OL is that the three-dimensional apertures 230 may create a void volume between the land area 250 of the garment-facing side of the topsheet 110 and a top surface of the fluid distribution material 140 or the absorbent core 130 (in embodiments that do not include a fluid distribution material 140) of the absorbent article 100. Such a void volume may improve the fluid handling properties of the topsheet 110, as compared to a topsheet that has two-dimensional apertures and a final loft that is the same as the original loft before aperturing.

Figure 5B:
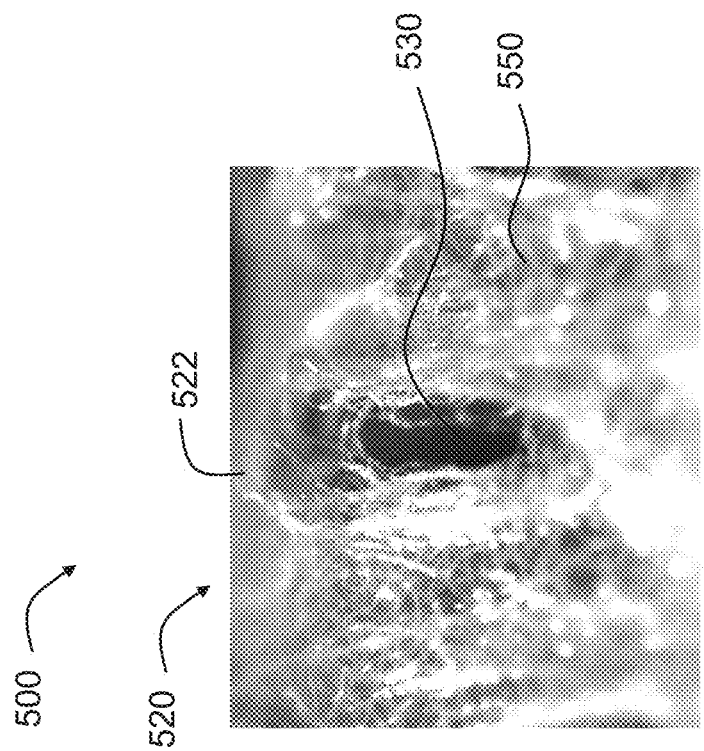
FIG. 5B is an enlarged view of a portion of a garment-facing side of the apertured extrusion coated nonwoven web of FIG. 5A.
Figure 5A:
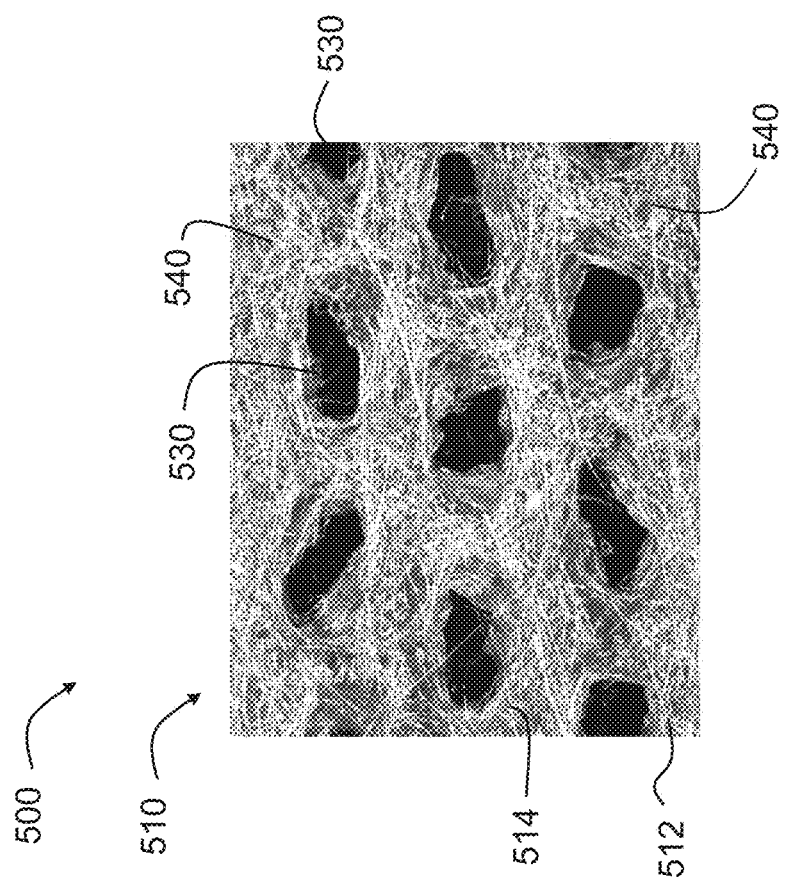
FIG. 5A is an enlarged view of a portion of a user-facing side of an apertured extrusion coated nonwoven web that may be used as a topsheet for the absorbent article of FIG. 1.

FIGS. 5A and 5B illustrate an apertured extrusion coated nonwoven web 500 according to an embodiment of the invention. FIG. 5A illustrates a user-facing side 510 and FIG. 5B illustrates a garment-facing side 520 of the apertured extrusion coated nonwoven web 500. The user-facing side 510 includes a nonwoven material 512 that includes a plurality of fibers 514. In this embodiment, the nonwoven material 512 is a carded nonwoven material and the plurality of fibers 514 are staple fibers. The garment-facing side 520 includes a polymer coating 522. A plurality of apertures 530 extend through the apertured extrusion coated nonwoven material 500 and are separated by a continuous land area 540 on the user-facing side 510 and a continuous land area 550 on the garment-facing side 520.

The fibers 214, 514 of the nonwoven materials 212, 512 may be made from one or more polyolefins, such as polypropylene, polyethylene, and/or combinations thereof, and/or may be made from one or more polyesters, such as polyethylene terephthalate ("PET"). In an embodiment, the fibers 214, 514 may be made from natural materials, such as cotton, hemp, or bamboo. In an embodiment, the fibers 214, 514 may be made from renewable bio-based materials, such as polyethylene or polypropylene made from sugar cane, or polylactic acid ("PLA"). In an embodiment, the fibers 214, 514 may be so-called bicomponent or "bi-co" fibers having a core made from one material and a sheath made from different material than the core material. In an embodiment, the nonwoven materials 212, 512 may have a basis weight of about 8 grams per square meter ("gsm") to about 50 gsm. In an embodiment, the nonwoven materials 212, 512 may have a basis weight of about 8 gsm to about 30 gsm. In an embodiment, the nonwoven materials 212, 512 may have a basis weight of about 10 gsm to about 15 gsm.

The polymer coatings 222, 522 may include one or more polyolefins, including but not limited to polyethylene, ultra-low density polyethylene, low density polyethylene, linear low density polyethylene, linear medium density polyethylene, high density polyethylene, polypropylene, ethylene-vinyl acetates, metallocene, as well as other polymers. Other polymers include but are not limited to elastomeric polymers, including but not limited to polypropylene based elastomers, ethylene based elastomers, copolyester based elastomers, olefin block copolymers, styrenic block copolymers and the like, or combinations thereof. In an embodiment, the polymer coatings 222, 522 may include a renewable bio-based material, such as polyethylene or polypropylene made from sugar cane, or polylactic acid ("PLA"). Additives, such as surfactants, fillers, colorants, opacifying agents and/or other additives known in the art may also be used in the polymer coatings 222, 522.

Figure 6:
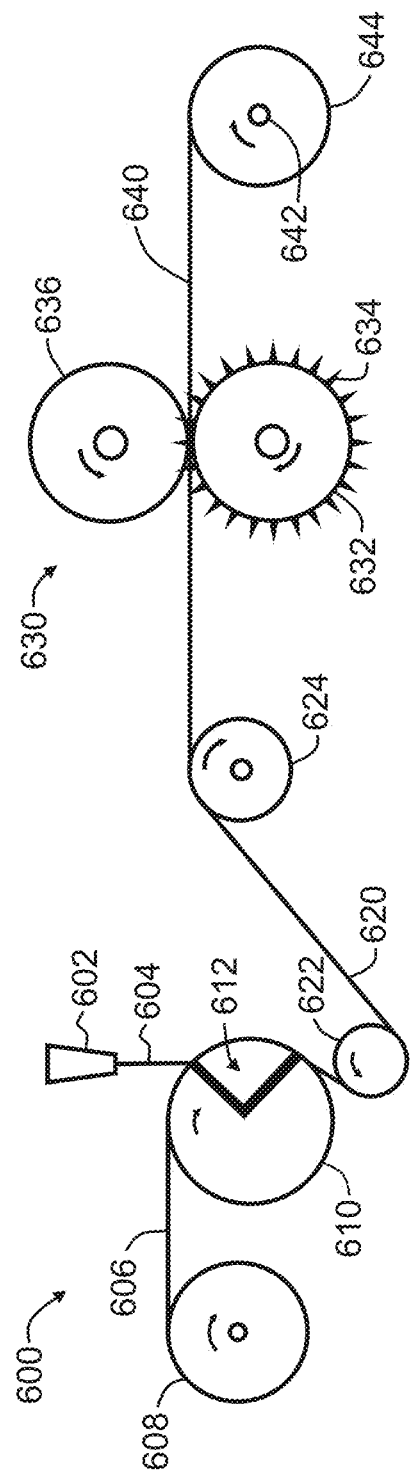
FIG. 6 is a schematic illustration of an apparatus for manufacturing apertured extrusion coated nonwoven webs in accordance with embodiments of the invention.

FIG. 6 schematically illustrates an apparatus 600 that may be used to manufacture the apertured extruded coated nonwoven webs 200, 500 of embodiments of the invention described herein. As illustrated, an extrusion die 602 extrudes a polymer melt curtain 604 onto a nonwoven web 606, which is unwound from a roll 608, as the nonwoven web 606 is fed over a forming structure 610 that rotates about a cylinder having a vacuum slot 612 through which a vacuum is pulled. The forming structure 610 includes a plurality of openings arranged in a pattern of between about 5 and about 120 openings per linear inch (i.e., about 5-120 mesh) The polymer melt curtain 604 may include, for example, one or more polyolefin materials, as well as one or more additives, such as a surfactant. As the nonwoven web 606 and polymer melt curtain 604 pass over the vacuum slot 612, the polymer in the melt curtain 604 coats the fibers of the nonwoven web 606 and the vacuum that is pulled through the vacuum slot 612 and forming structure 610 pulls the polymer against the nonwoven web 606 as the polymer cools. The resulting extrusion coated nonwoven web 620 having an original loft OL, described above, is pulled off of forming structure 610 by a peel roller 622 and travels to one or more additional rollers 624 and fed to a pin punching station 630. In an embodiment, a cast roll may be used in lieu of the forming structure 610 and cylinder having the vacuum slot 612, and the polymer melt curtain 604 may be applied to the nonwoven web 606 without the use of vacuum. The illustrated embodiment is not intended to be limiting in any way.

The pin punching station 630 includes a male roller 632 having a plurality of pins 634 extending from a circumference thereof, and a female roller 636 having complimentary recesses configured to receive the pins 634 of the male roller 632. The plurality of pins 634 initially contact the side of the extrusion coated nonwoven web 620 that includes the nonwoven web and pierce through the nonwoven web and the polymer coating to form three-dimensional apertures in the extrusion coated nonwoven web. After the three-dimensional apertures have been formed, the resulting apertured extrusion coated nonwoven web 640 having a final loft FL, described above, may be wound by a winder 642 into a roll 644. Additional rollers and/or other pieces of equipment may be used in the apparatus 600. The illustrated embodiment is not intended to be limiting in any way.

For example, in an embodiment, the apparatus 600 may also include additional equipment, such as intermeshing gears that may be used to activate the apertured extrusion coated nonwoven web 640 in the machine direction or the transverse direction, if desired. Other equipment that may be included in the apparatus 600 include, but are not limited to, corona treatment apparatus, printers, festooning equipment, spooling equipment, and additional processing equipment that may emboss or provide additional apertures to the apertured extrusion coated web 640. In an embodiment, a pair of embossing rollers may be located downstream of the pin punching station 630, either in-line or off-line.

In an embodiment, the extrusion coated nonwoven web 620 may be created and wound into a roll before being fed through the pin punch station 630, and later unwound and fed through a pin punch station that is not part of the apparatus 600, i.e. is off-line. In other words, the pin punch station 630 may not be in-line with the extrusion die 602 and the forming structure 610. In an embodiment, instead of being unwound from a roll 608 and fed to the forming structure 610, the nonwoven web may be made in-line and upstream of the forming structure 610. The illustrated embodiment is not intended to be limiting in any way.

EXAMPLES

Samples were made with the apparatus 600 of FIG. 6 to investigate the effects of the basis weight of the polymer coating, the type of nonwoven used for the nonwoven material, and the orientation of the extrusion coated nonwoven material relative to the male roller 632 and the female roller 636 of the pin punch station 630.

More specifically, a polymer blend of low density polyethyelene (LDPE), high density polyethyelene (HDPE), and a masterbatch including a surfactant was extruded at basis weights of 2 gsm, 4 gsm, 6 gsm, 8 gsm and 10 gsm onto a 10 gsm spunbond nonwoven material with polypropylene fibers and a 12 gsm carded nonwoven material with polypropylene fibers. The forming structure 610 had a plurality of openings in a pattern of about 40 openings per linear inch (i.e., about 40 mesh). The resulting extrusion coated nonwoven webs were apertured using the same pin punching station 630. The male roller 632 of the pin punching station 630 had an array of pins 634 spaced to provide a pattern of apertures having a mesh count of about 12 apertures per linear inch (i.e., about 12 mesh). One half of the extrusion coated nonwoven web 620 were apertured with the nonwoven material facing the male roller 632, resulting in the nonwoven material being on the female side of the apertured extrusion coated nonwoven web 640, and one half of the extrusion coated nonwoven web 620 were apertured with the nonwoven material facing the female roller 636, resulting in the nonwoven material being on the male side of the apertured extrusion coated nonwoven web 640. A summary of the samples that were made is listed in Table I below as Examples 1-20.

TABLE I

SUMMARY OF SAMPLES

| Example | Coating Basis Weight (gsm) | Nonwoven Basis Weight (gsm) | Nonwoven Type | Nonwoven Side |
|---|---|---|---|---|
| 1 | 2 | 10 | Spunbond | Female |
| 2 | 4 | 10 | Spunbond | Female |
| 3 | 6 | 10 | Spunbond | Female |
| 4 | 8 | 10 | Spunbond | Female |
| 5 | 10 | 10 | Spunbond | Female |
| 6 | 2 | 10 | Spunbond | Male |
| 7 | 4 | 10 | Spunbond | Male |
| 8 | 6 | 10 | Spunbond | Male |
| 9 | 8 | 10 | Spunbond | Male |
| 10 | 10 | 10 | Spunbond | Male |
| 11 | 2 | 12 | Carded | Female |
| 12 | 4 | 12 | Carded | Female |
| 13 | 6 | 12 | Carded | Female |
| 14 | 8 | 12 | Carded | Female |
| 15 | 10 | 12 | Carded | Female |
| 16 | 2 | 12 | Carded | Male |
| 17 | 4 | 12 | Carded | Male |
| 18 | 6 | 12 | Carded | Male |
| 19 | 8 | 12 | Carded | Male |
| 20 | 10 | 12 | Carded | Male |

A comparative polymer film having a basis weight of 22 gsm was also made using the same polymer blend and forming structure 610 that was used for apertured extrusion coated nonwoven web samples. Because the forming structure 610 had openings in a mesh pattern of about 40 mesh, the comparative polymer film had micro three-dimensional apertures in the same 40 mesh pattern before it was subjected to the pin punch station 630.

Open Area

The "Open Area" is the percent area of openings through the sample as compared to the total area of the sample. Because topsheets 110 of absorbent articles 100 are subjected to pressure when the user sits, for example, it is desirable for the three-dimensional apertures 230, 530 of the topsheet 110 to stay open as much as possible when subjected to pressure so that body exudates can still pass through the topsheet 110 to the absorbent core 130. The Open Area for each sample was measured using a computerized video device that includes a video camera, a microscope using a 24× magnification, and imaging software that measures contrast. A magnified image was taken of the sample when looking at the female side of the sample, and the video camera, which can discern the openings through the sample from the land areas 240, 540 of the sample via contrast, digitized the data to calculate the percent (%) Open Area. The Open Area was measured while the sample was under pressures of 0.0 psi, 0.2 psi, 0.4 psi, and 0.6 psi. After the pressure of 0.6 psi was relieved, the Open Area for the sample was measured again to see how much of the initial Open Area was recovered. Tables II-V summarize the Open Areas that were measured for each apertured extrusion coated nonwoven web sample.

TABLE II

OPEN AREA UNDER PRESSURE - 10 GSM SPUN
BOND NONWOVEN ON FEMALE SIDE (EXAMPLES 1-5)

| Example | Coating Basis Weight (gsm) | Initial Open Area (%) | Open Area Under 0.2 psi (%) | Open Area Under 0.4 psi (%) | Open Area Under 0.6 psi (%) | Open Area After Pressure Relieved (%) |
|---|---|---|---|---|---|---|
| 1 | 2 | 13.6 | 10.6 | 10.2 | 10.1 | 12.0 |
| 2 | 4 | 13.0 | 9.2 | 8.1 | 7.7 | 10.6 |
| 3 | 6 | 13.1 | 8.3 | 5.6 | 5.3 | 9.0 |
| 4 | 8 | 12.6 | 6.0 | 3.4 | 2.6 | 7.3 |
| 5 | 10 | 10.9 | 5.3 | 2.9 | 1.9 | 6.0 |

Figure 7:
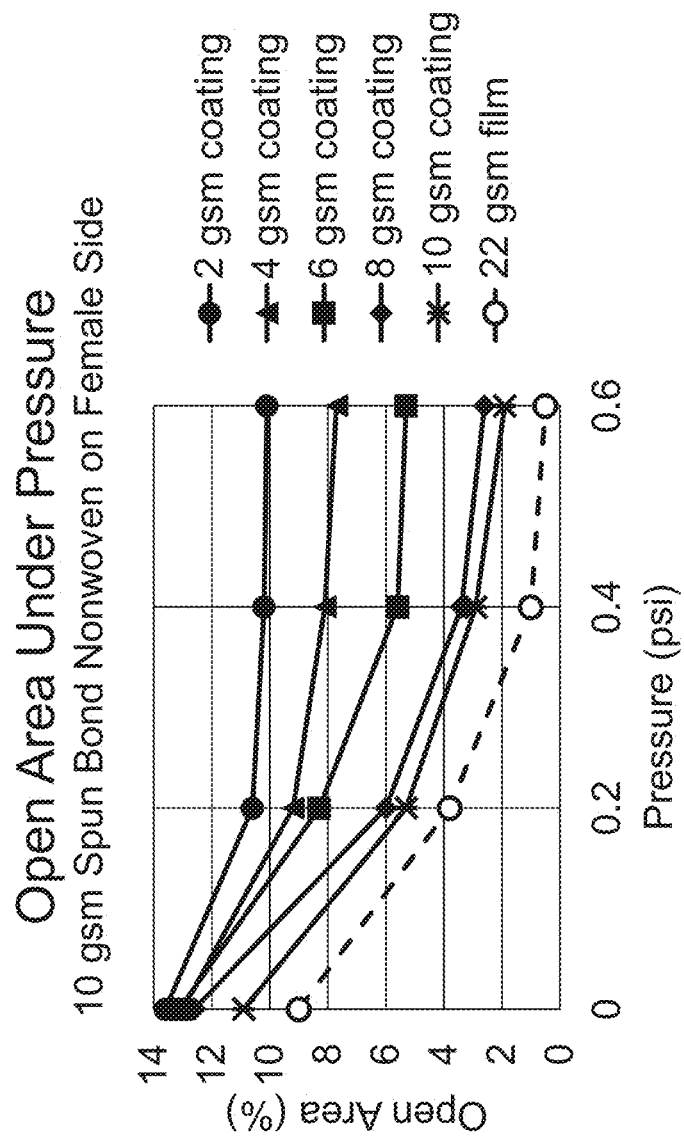
FIG. 7 is a graph of open area as a function of applied pressure for a series of apertured extrusion coated nonwoven webs that may be used as a topsheet for the absorbent article of FIG. 1.

The results listed in Table II, with the exception of "Open Area After Pressure Relieved" are also illustrated in FIG. 7, along with the measured Open Area of the comparative 22 gsm film sample. As illustrated, the Open Area decreased as the pressure applied to the sample increased. The results also indicate that the Open Area of the samples generally decreased as the basis weight of the polymer coating increased at a given pressure.

TABLE III

OPEN AREA UNDER PRESSURE - 10 GSM SPUN
BOND NONWOVEN ON MALE SIDE (EXAMPLES 6-10)

| Example | Coating Basis Weight (gsm) | Initial Open Area (%) | Open Area Under 0.2 psi (%) | Open Area Under 0.4 psi (%) | Open Area Under 0.6 psi (%) | Open Area After Pressure Relieved (%) |
|---|---|---|---|---|---|---|
| 6 | 2 | 6.7 | 4.7 | 4.5 | 4.4 | 5.2 |
| 7 | 4 | 5.1 | 3.6 | 3.3 | 3.2 | 4.0 |
| 8 | 6 | 5.0 | 2.6 | 2.2 | 2.0 | 3.2 |
| 9 | 8 | 4.7 | 1.7 | 1.2 | 1.1 | 2.3 |
| 10 | 10 | 4.1 | 1.5 | 1.0 | 0.8 | 2.1 |

Figure 8:
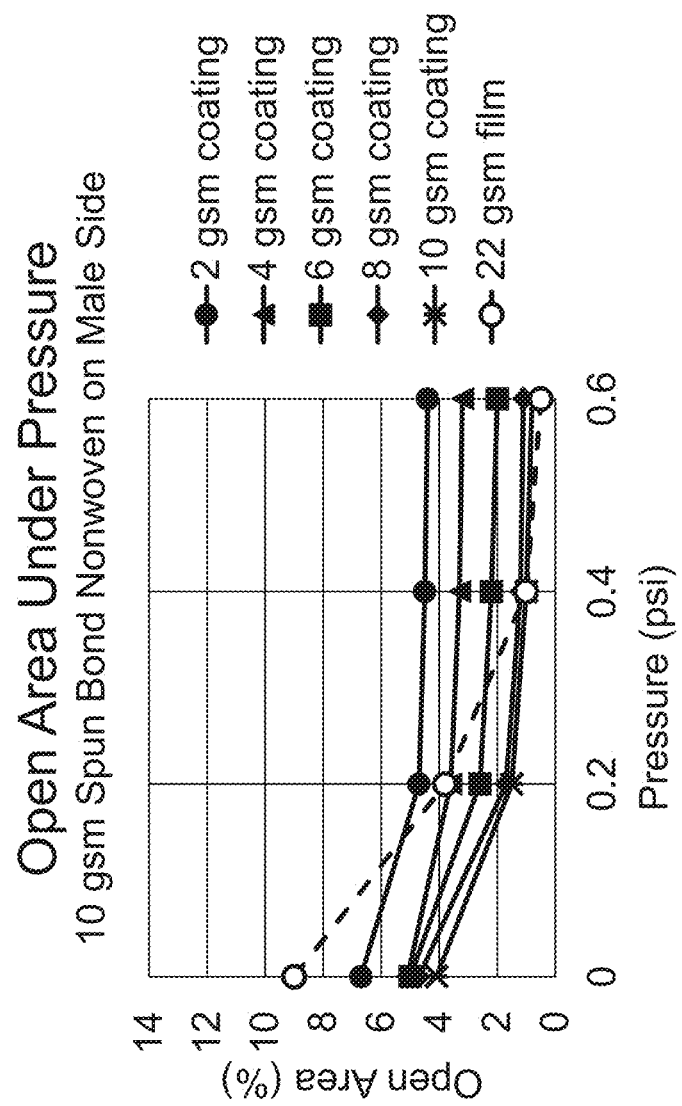
FIG. 8 is a graph of open area as a function of applied pressure for a series of apertured extrusion coated nonwoven webs that may be used as a topsheet for the absorbent article of FIG. 1.

The results listed in Table III, with the exception of "Open Area After Pressure Relieved" are also illustrated in FIG. 8, along with the measured Open Area of the comparative 22 gsm film sample. As illustrated, the Open Area decreased as the pressure applied to the sample increased, although the Open Area for each example substantially levelled off at the higher pressures. The results also indicate that the Open Area of the samples generally decreased as the basis weight of the polymer coating increased at a given pressure. A comparison of FIGS. 7 and 8 indicates that the for each polymer coating basis weight, the samples having the nonwoven material on the female side of the apertured extrusion coated nonwoven web had higher Open Areas than the samples having the nonwoven material on the male side of the apertured extrusion coated nonwoven web.

TABLE IV

OPEN AREA UNDER PRESSURE - 12 GSM CARDED
NONWOVEN ON FEMALE SIDE (EXAMPLES 11-15)

| Example | Coating Basis Weight (gsm) | Initial Open Area (%) | Open Area Under 0.2 psi (%) | Open Area Under 0.4 psi (%) | Open Area Under 0.6 psi (%) | Open Area After Pressure Relieved (%) |
|---|---|---|---|---|---|---|
| 11 | 2 | 9.5 | 6.6 | 6.2 | 6.1 | 7.3 |
| 12 | 4 | 10.3 | 6.8 | 6.1 | 5.8 | 8.0 |
| 13 | 6 | 11.0 | 8.2 | 6.2 | 5.6 | 8.6 |
| 14 | 8 | 11.3 | 7.7 | 4.9 | 3.8 | 8.3 |
| 15 | 10 | 13.6 | 10.2 | 6.2 | 4.1 | 9.5 |

Figure 9:
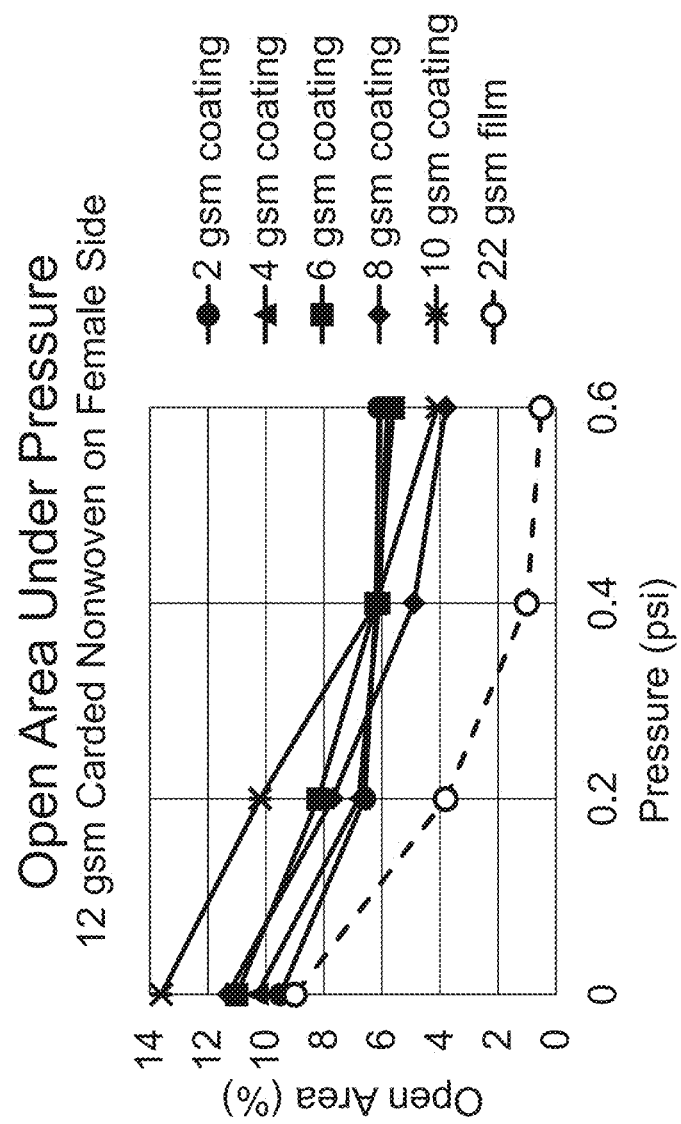
FIG. 9 is a graph of open area as a function of applied pressure for a series of apertured extrusion coated nonwoven webs that may be used as a topsheet for the absorbent article of FIG. 1.

The results listed in Table IV, with the exception of "Open Area After Pressure Relieved" are also illustrated in FIG. 9, along with the measured Open Area of the comparative 22 gsm film sample. As illustrated, the Open Area decreases as the pressure applied to the sample increases. The results also indicate that although the initial Open Areas of the samples having higher basis weights of the polymer coating were higher than the other samples, the Open Areas under 0.6 psi were higher for the samples having lower basis weights of the polymer coating.

TABLE V

OPEN AREA UNDER PRESSURE - 12 GSM CARDED
NONWOVEN ON MALE SIDE (EXAMPLES 16-20)

| Example | Coating Basis Weight (gsm) | Initial Open Area (%) | Open Area Under 0.2 psi (%) | Open Area Under 0.4 psi (%) | Open Area Under 0.6 psi (%) | Open Area After Pressure Relieved (%) |
|---|---|---|---|---|---|---|
| 16 | 2 | 10.0 | 6.9 | 6.6 | 6.5 | 7.4 |
| 17 | 4 | 8.5 | 5.8 | 5.5 | 5.3 | 6.6 |
| 18 | 6 | 8.3 | 5.4 | 4.6 | 4.3 | 6.4 |
| 19 | 8 | 7.2 | 3.9 | 2.7 | 2.4 | 4.6 |
| 20 | 10 | 8.5 | 4.5 | 2.7 | 2.2 | 4.8 |

Figure 10:
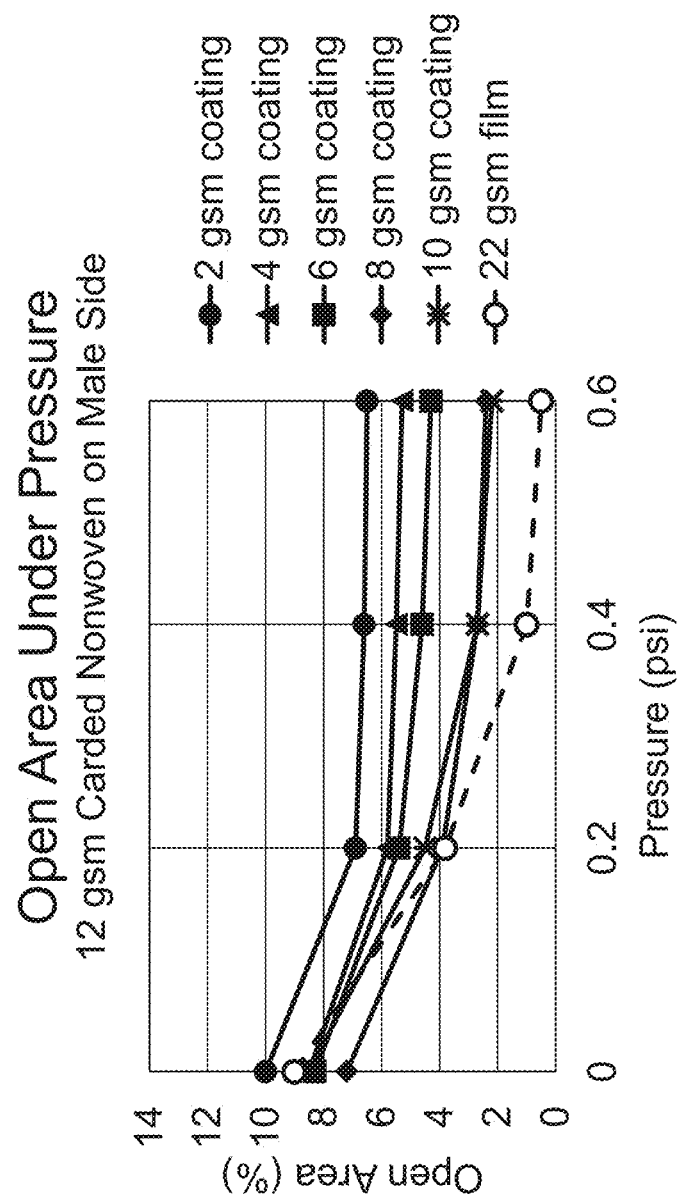
FIG. 10 is a graph of open area as a function of applied pressure for a series of apertured extrusion coated nonwoven webs that may be used as a topsheet for the absorbent article of FIG. 1.

The results listed in Table V, with the exception of "Open Area After Pressure Relieved" are also illustrated in FIG. 10, along with the measured Open Area of the comparative 22 gsm film sample. As illustrated, the Open Area decreases as the pressure applied to the sample increases. The results also indicate that the Open Area of the samples generally decreases as the basis weight of the polymer coating increases, particularly under pressure.

For each applied pressure, as well as after the pressure was relieved, the percentage of the initial Open Area (i.e., the Open Area at 0.0 psi applied pressure) was calculated. Tables VI-IX summarize the results of the calculations.

TABLE VI

PERCENTAGE OF INITIAL OPEN AREA UNDER
PRESSURE - 10 GSM SPUN BOND NONWOVEN
ON FEMALE SIDE (EXAMPLES 1-5)

| Example | Coating Basis Weight (gsm) | % Initial Open Area Under 0.2 psi (%) | % Initial Open Area Under 0.4 psi (%) | % Initial Open Area Under 0.6 psi (%) | % Initial Open Area After Pressure Relieved (%) |
|---|---|---|---|---|---|
| 1 | 2 | 77.9 | 75.0 | 74.3 | 88.2 |
| 2 | 4 | 70.8 | 62.3 | 59.2 | 81.5 |
| 3 | 6 | 63.4 | 42.7 | 40.5 | 68.7 |
| 4 | 8 | 47.6 | 27.0 | 20.6 | 57.9 |
| 5 | 10 | 48.6 | 26.6 | 17.4 | 55.0 |

The results listed in Table VI indicate that as the basis weight of the polymer coating increased, the amount of Open Area maintained by the apertured extrusion coated nonwoven web decreased. In addition, after the 0.6 psi applied pressure was relieved, the amount of Open Area that was recovered increased as the basis weight of the polymer coating decreased.

TABLE VII

PERCENTAGE OF INITIAL OPEN AREA UNDER PRESSURE - 10 GSM SPUN BOND NONWOVEN ON MALE SIDE (EXAMPLES 6-10)

| Example | Coating Basis Weight (gsm) | % Initial Open Area Under 0.2 psi (%) | % Initial Open Area Under 0.4 psi (%) | % Initial Open Area Under 0.6 psi (%) | % Initial Open Area After Pressure Relieved (%) |
|---|---|---|---|---|---|
| 6 | 2 | 70.1 | 67.2 | 65.7 | 77.6 |
| 7 | 4 | 70.6 | 64.7 | 62.9 | 78.4 |
| 8 | 6 | 52.0 | 44.0 | 40.0 | 64.0 |
| 9 | 8 | 36.2 | 25.5 | 23.4 | 48.9 |
| 10 | 10 | 36.6 | 24.4 | 19.5 | 51.2 |

The results listed in Table VII indicate that as the basis weight of the polymer coating increased, the amount of Open Area maintained by the apertured extrusion coated nonwoven web decreased. In addition, after the 0.6 psi applied pressure was relieved, the amount of Open Area that was recovered generally increased as the basis weight of the polymer coating decreased.

TABLE VIII

PERCENTAGE OF INITIAL OPEN AREA UNDER PRESSURE - 12 GSM CARDED NONWOVEN ON FEMALE SIDE (EXAMPLES 11-15)

| Example | Coating Basis Weight (gsm) | % Initial Open Area Under 0.2 psi (%) | % Initial Open Area Under 0.4 psi (%) | % Initial Open Area Under 0.6 psi (%) | % Initial Open Area After Pressure Relieved (%) |
|---|---|---|---|---|---|
| 11 | 2 | 69.5 | 65.3 | 64.2 | 76.8 |
| 12 | 4 | 66.0 | 59.2 | 56.3 | 77.7 |
| 13 | 6 | 74.5 | 56.4 | 50.9 | 78.2 |
| 14 | 8 | 68.1 | 43.4 | 33.6 | 73.5 |
| 15 | 10 | 75.0 | 45.6 | 30.1 | 69.8 |

The results listed in Table VIII indicate that as the basis weight of the polymer coating increased, the amount of Open Area maintained by the apertured extrusion coated nonwoven web decreased at the higher pressures. In addition, after the 0.6 psi applied pressure was relieved, the amount of Open Area that was recovered generally increased as the basis weight of the polymer coating decreased.

TABLE IX

PERCENTAGE OF INITIAL OPEN AREA UNDER PRESSURE - 12 GSM CARDED NONWOVEN ON MALE SIDE (EXAMPLES 16-20)

| Example | Coating Basis Weight (gsm) | % Initial Open Area Under 0.2 psi (%) | % Initial Open Area Under 0.4 psi (%) | % Initial Open Area Under 0.6 psi (%) | % Initial Open Area After Pressure Relieved (%) |
|---|---|---|---|---|---|
| 16 | 2 | 69.0 | 66.0 | 64.2 | 74.0 |
| 17 | 4 | 68.2 | 64.7 | 62.4 | 77.6 |
| 18 | 6 | 65.1 | 55.4 | 51.8 | 77.1 |
| 19 | 8 | 54.2 | 37.5 | 33.3 | 63.9 |
| 20 | 10 | 52.9 | 31.8 | 25.9 | 56.5 |

The results listed in Table IX indicate that as the basis weight of the polymer coating increased, the amount of Open Area maintained by the apertured extrusion coated nonwoven web decreased. In addition, after the 0.6 psi applied pressure was relieved, the amount of Open Area that was recovered increased as the basis weight of the polymer coating decreased.

Strikethrough Time and Rewet Testing

Each of Examples 1-20 was tested for suitability for use as the topsheet 110 in the absorbent article 100. Specifically, for each sample, a Strikethrough Time, which is a measure of how fast liquid passes through the topsheet 110, and Rewet Value, which is a measure of dryness, were determined for three different test specimens by a "Lister AC" fluid testing device, by Lenzing Technik GmbH & Co KG, Austria. The procedures for measuring strikethrough time ("Strikethrough Test Method") and rewet ("Rewet Test Method"), which are based on the principles outlined in EDANA test methods ERT 150.5-02 and ERT 151.3-02, respectively, will now be described. All of the test specimens and absorbent substrates, filter papers and pickup papers described below were conditioned at 23° C.±2° C. at 50%±5% relative humidity for 24 hours.

For the Strikethrough Test Method, each test specimen was cut into a 5"×5" (125 mm×125 mm) piece and placed over an absorbent substrate in the form of a stack of three (3) pieces of 4"×4" filter (blotter) paper. The test specimen was oriented so that the female side faced upward and the male side was in contact with the filter paper. A 500 g strikethrough plate with a 100 mm×100 mm base dimension and an orifice with electrodes extending into the orifice was placed on top of the test specimen. A 5 mL sample of fluid that simulates urine and consists of a solution of 9.0 g/l of analytical grade sodium chloride in deionized water, with a surface tension of 70±2 mN/m at 23±2° C., was dispersed into the orifice from a height of 30 mm above the surface of the test specimen. The fluid completed a circuit with the electrodes, which started a timer. When the fluid was completely struck through the orifice, the circuit was broken and the timer stopped, thereby registering the elapsed time or "Strikethrough Time" in seconds. The average strikethrough time test results for three test specimens for each sample are listed in below in Table X.

For the "Rewet Test Method," after the initial insult from the Strikethrough Test Method, an additional insult was dispensed to the center of the test specimen with the strikethrough plate still in place. The additional insult was based on the total insult (including the initial 5 mL insult from the Strikethrough Test Method) needed to fully saturate the underlying absorbent substrate and was calculated by multiplying the weight of the stack of three pieces of filter paper (when dry) by the load factor of the filter paper, and was determined to be 10 mL. The strikethrough plate was removed and a 4000 g rewet weight with a 100 mm×100 mm footing was placed on top of the test specimen to allow the fluid to thoroughly spread out into the absorbent substrate. Two pre-weighed 5"×5" pick up (blotter) papers were pressed against the surface of the test specimen with the rewet weight to create a pressure of about 0.50 psi, to simulate a toddler sitting on a diaper, for an additional two minutes. The wetted pickup papers were weighed. Any residual wetness in the test specimen is transferred to the pickup papers, and the difference between the pre-measured dry weight of the pickup papers and the wetted weight of the pickup papers is the "Rewet Value" in grams. The average rewet value test results for three test specimens for each sample are also listed below in Table X.

TABLE X

STRIKETHROUGH TIME AND REWET TEST RESULTS

| Example | Strikethrough Time (sec) | Rewet Value (g) |
|---|---|---|
| 1 | 5.8 | 0.16 |
| 2 | 6.1 | 0.11 |
| 3 | 6.0 | 0.09 |
| 4 | 5.8 | 0.05 |
| 5 | 4.9 | 0.04 |
| 6 | 6.1 | 0.63 |
| 7 | 7.8 | 0.16 |
| 8 | 6.6 | 0.11 |
| 9 | 4.6 | 0.05 |
| 10 | 5.2 | 0.06 |
| 11 | 4.0 | 2.99 |
| 12 | 3.4 | 2.23 |
| 13 | 2.3 | 2.28 |
| 14 | 2.0 | 1.67 |
| 15 | 1.9 | 1.51 |
| 16 | 3.3 | 2.98 |
| 17 | 3.5 | 2.92 |
| 18 | 3.1 | 2.32 |
| 19 | 3.0 | 1.04 |
| 20 | 2.1 | 0.68 |

Figure 11:
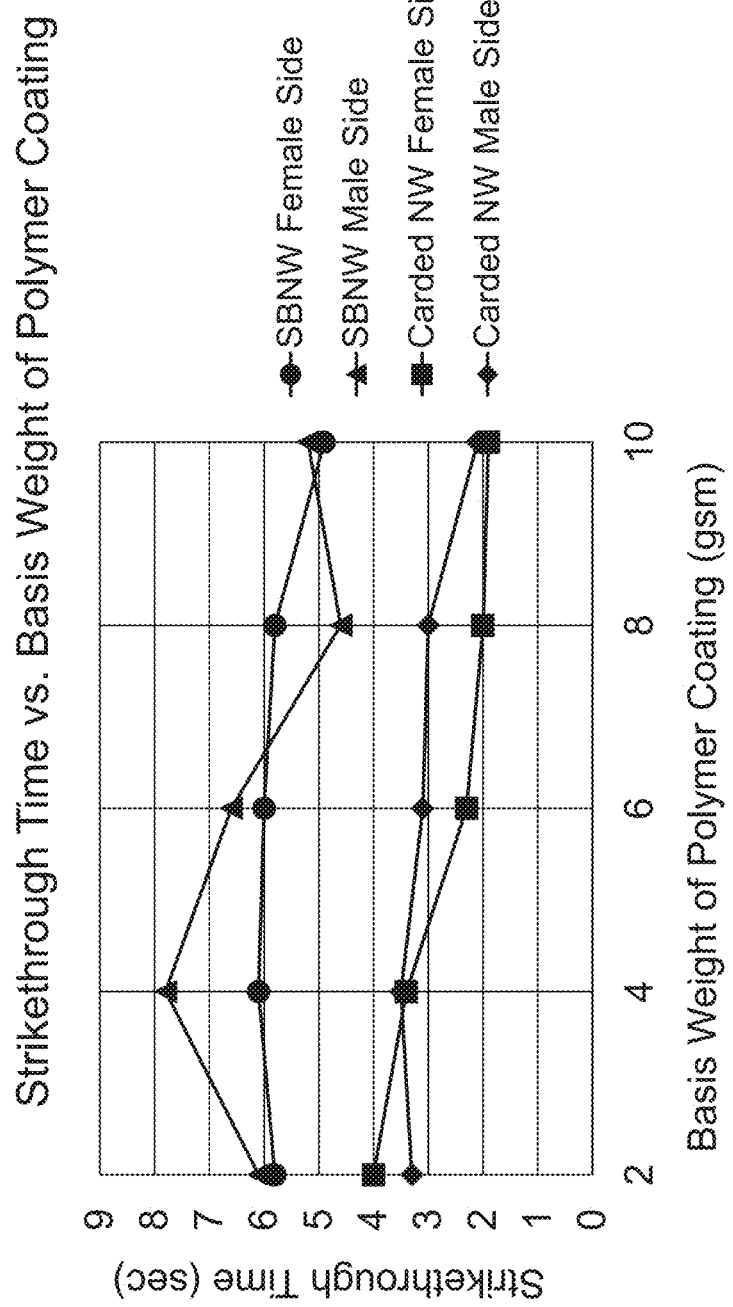
FIG. 11 is a graph of strikethrough times as a function of coating basis weight for multiple series of apertured extrusion coated nonwoven webs that may be used as a topsheet for the absorbent article of FIG. 1.
Figure 12:
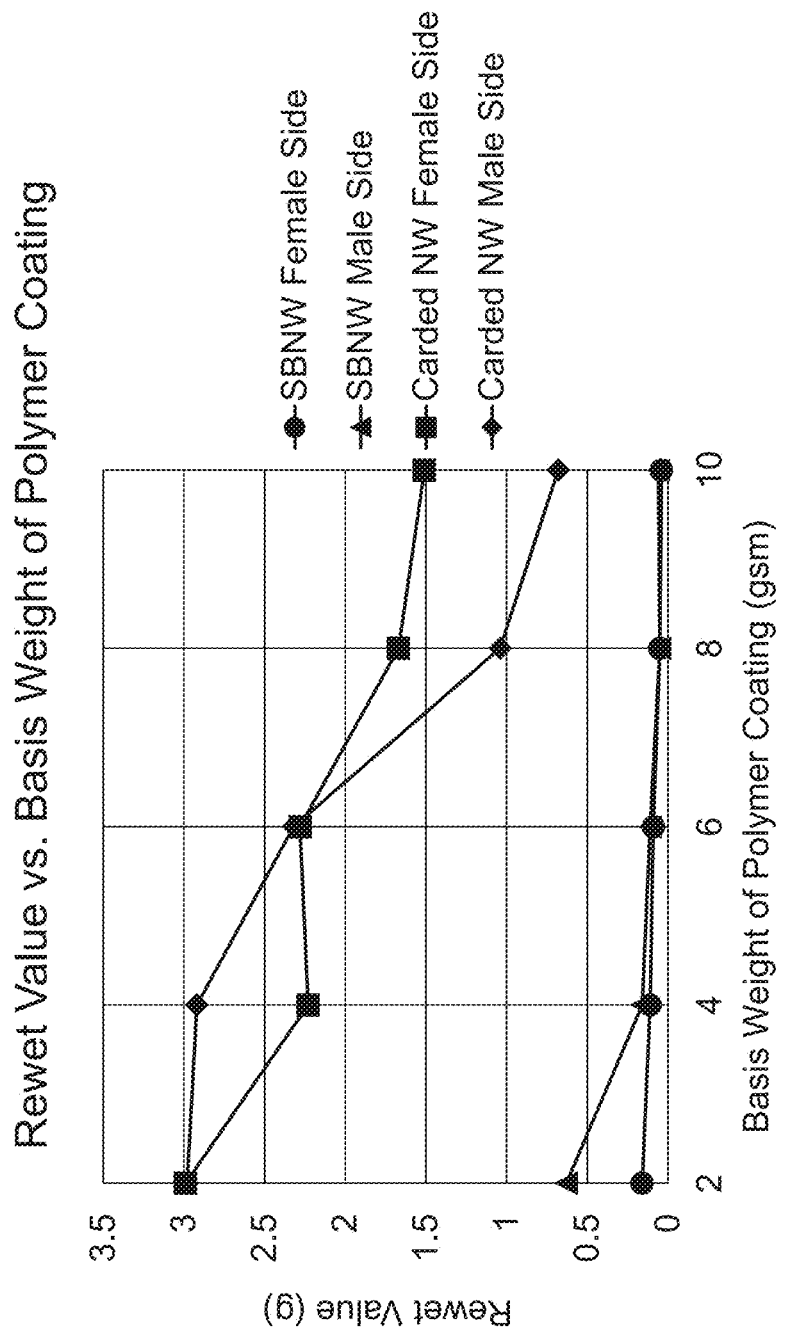
FIG. 12 is a graph of rewet values as a function of coating basis weight for multiple series of apertured extrusion coated nonwoven webs that may be used as a topsheet for the absorbent article of FIG. 1.

The Strikethrough Time results are illustrated in FIG. 11 and the Rewet Value results are illustrated in FIG. 12. Examples 1-10, which had the spunbond nonwoven material, had higher Strikethrough Times and significantly lower Rewet Values than Examples 11-20, which had the carded nonwoven material. In addition, the Rewet Values generally decreased as the basis weight of the polymer coating increased for each of the four constructions.

The embodiments described herein represent a number of possible implementations and examples and are not intended to necessarily limit the present disclosure to any specific embodiments. Instead, various modifications can be made to these embodiments, and different combinations of various embodiments described herein may be used as part of the invention, even if not expressly described, as would be understood by one of ordinary skill in the art. Any such modifications are intended to be included within the spirit and scope of the present disclosure and protected by the following claims.

What is claimed is:

1. An apertured extrusion coated nonwoven web for use as a topsheet in an absorbent article, the extrusion coated nonwoven web comprising:
a nonwoven material having a user-facing side and a garment-facing side opposite the user-facing side, the nonwoven material comprising a plurality of fibers;
a polymer coating on the garment-facing side of the nonwoven material, the polymer coating having a basis weight of about 2 gsm to about 6 gsm; and
a plurality of three-dimensional apertures extending through the nonwoven material and the polymer coating, each of the plurality of three-dimensional apertures comprising a continuous sidewall extending from a garment-facing side of the polymer coating,
wherein the three-dimensional apertures are arranged in a pattern of about 5 mesh to about 30 mesh,
wherein the continuous sidewall comprises both the nonwoven material and the polymer coating, and
wherein the apertured extrusion coated nonwoven web has an open area of greater than 5% when subjected to a pressure of 0.6 psi.

2. The apertured extrusion coated nonwoven web according to claim 1, wherein the apertured extrusion coated nonwoven web has an open area of at least 50% of an original open area after the pressure of 0.6 psi is decreased to 0.0 psi.

3. The apertured extrusion coated nonwoven web according to claim 1, wherein the apertured extrusion coated nonwoven web has an original open area of about 9% to about 15%.

4. The apertured extrusion coated nonwoven web according to claim 1, wherein the nonwoven material is a spunbond nonwoven material and the fibers are continuous fibers.

5. The apertured extrusion coated nonwoven web according to claim 1, wherein the nonwoven material is a carded nonwoven material and the fibers are staple fibers.

6. The apertured extrusion coated nonwoven web according to claim 1, wherein the nonwoven material has a basis weight of about 8 gsm to about 20 gsm.

7. The apertured extrusion coated nonwoven web according to claim 6, wherein the nonwoven material has a basis weight of about 10 gsm to about 15 gsm.

8. The apertured extrusion coated nonwoven web according to claim 1, wherein the polymer coating comprises polyethylene.

9. The apertured extrusion coated nonwoven web according to claim 8, wherein the polymer coating comprises high density polyethylene.

10. The apertured extrusion coated nonwoven web according to claim 1, wherein the polymer coating has a basis weight of about 4 gsm to about 6 gsm.

11. The apertured extrusion coated nonwoven web according to claim 1, wherein the apertures are arranged in a pattern of about 10 mesh to about 15 mesh.

12. An absorbent article comprising:
a user-facing topsheet;
a garment-facing backsheet; and
an absorbent core in between the topsheet and the backsheet,
wherein the topsheet comprises an apertured extrusion coated nonwoven web comprising
a nonwoven material having a user-facing side and a garment-facing side opposite the user-facing side, the nonwoven material comprising a plurality of fibers;
a polymer coating on the garment-facing side of the nonwoven material, the polymer coating having a basis weight of about 2 gsm to about 6 gsm; and
a plurality of three-dimensional apertures extending through the nonwoven material and the polymer coating, each of the plurality of three-dimensional apertures comprising a continuous sidewall extending from a garment-facing side of the polymer coating,
wherein the three-dimensional apertures are arranged in a pattern of about 5 mesh to about 30 mesh,
wherein the continuous sidewall comprises both the nonwoven material and the polymer coating, and
wherein the apertured extrusion coated nonwoven web has an open area of greater than 5% when subjected to a pressure of 0.6 psi.

13. A method for making apertured extrusion coated nonwoven web for use as a topsheet in an absorbent article, the method comprising:
   extruding a polymer coating having a basis weight of about 2 gsm to about 6 gsm onto a nonwoven material to form an extrusion coated nonwoven web;
   pin punching a plurality of three-dimensional apertures through the extrusion coated nonwoven web to form an apertured extrusion coated nonwoven web, each of the plurality of three-dimensional apertures comprising a continuous sidewall extending from a garment-facing side of the polymer coating,
   wherein the three-dimensional apertures are arranged in a pattern of about 5 mesh to about 30 mesh,
   wherein the continuous sidewall comprises both the nonwoven material and the polymer coating, and
   wherein the apertured extrusion coated nonwoven web has an open area of greater than 5% when subjected to a pressure of 0.6 psi.

14. The method according to claim 13, wherein the polymer coating is extruded onto the nonwoven material as the nonwoven material is fed over a forming structure that rotates about a cylinder having a vacuum slot through which a vacuum is pulled.

15. The method according to claim 13, further comprising activating the apertured extrusion coated nonwoven web.

16. The method according to claim 13, further comprising embossing the apertured extrusion coated nonwoven web.

* * * * *